United States Patent [19]

Hartless et al.

[11] 4,073,771

[45] Feb. 14, 1978

[54] STABILIZED POLYMERIC COMPOSITION AND PRODUCT USING SAME

[75] Inventors: Ray Lawson Hartless, Lopatcong Township, Warren County, N.J.; Anthony Marion Trozzolo, South Bend, Ind.

[73] Assignee: Bell Telephone Laboratories, Incorporated, Murray Hill, N.J.

[21] Appl. No.: 709,603

[22] Filed: July 29, 1976

Related U.S. Application Data

[63] Continuation-in-part of Ser. No. 500,957, Aug. 27, 1974, abandoned.

[51] Int. Cl.$^2$ ............................................... C08K 5/20
[52] U.S. Cl. ..................... 260/45.9 NC; 174/110 PM; 260/438.1; 260/559 A; 260/559 H; 428/379; 428/461
[58] Field of Search .......... 260/45.9, 45.9 NC, 559 A, 260/559 H, 438.1

[56] References Cited

U.S. PATENT DOCUMENTS

| | | | |
|---|---|---|---|
| 3,357,944 | 12/1967 | Dexter | 260/45.9 |
| 3,734,884 | 5/1973 | Dunnenberger et al. | 260/45.9 NC |
| 3,870,680 | 3/1975 | Schurdak | 260/45.9 NC |
| 3,894,083 | 7/1975 | Hofer et al. | 260/45.9 NC |

*Primary Examiner*—Donald E. Czaja
*Assistant Examiner*—H. H. Fletcher
*Attorney, Agent, or Firm*—George S. Indig; Bruce S. Schneider

[57] ABSTRACT

The condensation products of oxalyl dihydrazide and 3,5-di-tertiary-butyl-4-hydroxy aryl carbonyl compounds are found to stabilize polyethylene against oxidative degradation. Stabilizer effectiveness is retained with the polymer in contact with copper. Stabilized polymers are effectively utilized as wire insulation.

5 Claims, No Drawings

STABILIZED POLYMERIC COMPOSITION AND PRODUCT USING SAME

CROSS REFERENCE TO RELATED APPLICATIONS

This application is a continuation-in-part application, from copending application, Ser. No. 500,957 filed Aug. 27, 1974, now abandoned.

BACKGROUND OF THE INVENTION

1. Field of the Invention

The invention is concerned with the stabilization of essentially saturated hydrocarbon polymeric materials against oxidative degradation and is particularly concerned with such stabilization under circumstances that the polymer is in intimate contact with copper or other metals known to accelerate the oxidative degradative process.

2. Description of the Prior Art

It is well recognized that saturated hydrocarbon polymeric compositions degrade under the influence of oxygen. This degradation which involves mechanical as well as electrical properties increases with increasing temperature and is, accordingly, known as thermal degradation. It is also well known that the degradative process is accelerated by the presence of copper and certain other active materials. The degradative process is believed initiated at the sites of tertiary carbon atoms on the polymer chain and, accordingly, is more pronounced, for example, in polypropylene which, by its nature, contains a tertiary carbon for every two carbons in the main chain, than in polyethylene which may contain only from 1/50 to 1/1000 tertiary carbons expressed as a fraction of the total number of carbon atoms in the polymer chain.

The thermal oxidative degradation process in polyolefins is considered to be autocatalytic, proceeding from the production of free radicals resulting from hydroperoxide production. Catalysts of the degradative process by copper or other metal ions is thought to proceed by the formation of unstable coordination complexes which facilitate free radical production.

Thermal degradative effects are minimized in such compositions generally by any of a class of hindered phenols or aryl amines which combine with free radicals to act as chain terminators. A large variety of such "thermal antioxidants" are commercially available and any of several provide adequate protection for many uses. Nevertheless, there is some continuing effort to develop new antioxidants, sometimes for economic reasons, sometimes to minimize effect on certain polymer properties, and, always, to still further extend lifetime.

An area of some continued activity concerns well engineered, long life expectancy polymeric products which are necessarily maintained in contact with copper or other active metals known to accelerate degradation. Perhaps the most prevalent category is that of primary insulation on copper wire (although similar effects are seen to a lesser extent where copper is replaced by other conductive metals, such as, aluminum). The effect of copper is lessened by any of several metal deactivators which somehow chemically combine with the metal ions. Oxamide, as well as some of its derivatives, accomplishes this end and has been used successfully in polymers including polypropylene and polyethylene. See 5, Polymer Engineering and Science 3 (1965). Another class of metal inhibitors is made up of the reaction products of an orthohydroxy aromatic carbonyl compound with an alkyl diamine. A more recently developed class of compounds, now in prevalent use in polyethylene, includes the reaction product of benzaldehyde and oxalyl dihydrazide. Such compounds, as represented by N,N'-dibenzal (oxalyl dihydrazide), are now in widespread use in polyethylene and ethylene propylene primary insulation. See U.S. Pat. No. 3,440,210. In general, where particularly long life is required, such protected compositions contain both a metal deactivator and a conventional thermal antioxidant.

SUMMARY OF THE INVENTION

A class of compounds has been found which stabilizes polyolefin compositions--e.g., compositions primarily consisting of homopolymers of ethylene and propylene, as well as copolymers such as that of ethylene and propylene. Stabilization is reasonably effective against degradative effects due to thermal oxidation and is to some extent also effective where the polymer is in intimate contact with copper or other active metal known to accelerate such degradation. Stabilizers of the inventive class are condensation products of oxalyl dihydrazide and 3-tertiary butyl-4 hydroxy aryl carbonyl compounds as exemplified by 3,5-di-tertiary-butyl-4-hydroxy benzaldehyde. Accelerated oxygen uptake tests conducted under a variety of conditions indicate members of the inventive stabilizing group to be excellent thermal antioxidants, perhaps comparable with the best commercial materials. While such stabilizers continue to be effective in the presence of copper and while they are superior to conventional thermal antioxidants in this respect, they are not, generally, to be compared with the best of the commercial metal inhibitors. The inventive stabilizers are chemically related to the N,N'-dibenzal-(oxalyl dihydrazide) of U.S. Pat. No. 3,440,210 but stabilizer effectiveness is quite different. The inventive materials are far superior to the prior art compound as thermal antioxidants whereas the prior art compound is somewhat better as a metal deactivator.

DETAILED DESCRIPTION

1. Composition

A. Novel Stabilizer

Compositions of the invention may be represented by the structural formula

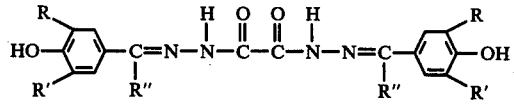

in which R is an alkyl substituent containing a tertiary carbon; in which R' is hydrogen or an alkyl substituent which may also contain a tertiary carbon; and in which R" is hydrogen or an alkyl substituent. To the extent that this class of stabilizers is dependent upon the hydroxyl substituent on the cyclic moiety other compositional considerations are common to those which apply to conventional phenolic stabilizers. So, for example, it is permitted to include alkyl or other ring substituents at positions for which no substituents are shown, as well as for the R' position, providing such substituents do not unduly sterically hinder, chemically combine with, or otherwise interfere with the activity of the hydroxyl or other active portion of the molecule. Also to be avoided are substituents which themselves have a deleterious effect on the polymer to be protected. Examples of groupings known to be harmful to effectiveness of hydroxyl groupings in their function of chain termination/free radical scavaging are nitro, nitroso, COOH, etc. Compositions of the invention are invariably condensation products involving oxalyl dihydrazide. While, from a functional standpoint, there may be variations in this reactant, i.e., addition of substituents, increase in chain length, etc, experiments to date impose further restraints based on such practical consideration as feasible condensation reactivity. The other reactant may be any of a class of aryl carbonyl materials, providing that there is a hydroxyl in a position para to a aldehyde or ketone group and poviding there is a substituent in a position ortho to the hydroxyl substituent which contains a tertiary carbon bonded directly to the cyclic moiety.

An example of such a compound is bis(3,5-di-tertiarybutyl-4-hydroxy benzaldehyde)oxalyl dihydrazide.

B. The Polymer

Polymeric compositions beneficially stabilized in accordance with the invention are nominally ethylenically saturated. They may be homopolymers, such as, polyethylene, polypropylene, poly-butene-1 etc; they may be copolymers, such as, poly (ethylene-propylene). From the thermal oxidative standpoint, it is now well established that a region of susceptibility in the polymer is that containing a tertiary carbon atom. First attack may also involve an occasional (nominally absent) ethylenic unsaturation as well as certain impurities, such as, residual catalyst originally introduced to bring about polymerization (particularly in high density Ziegler-type polymers).

While discussion is generally in terms of prototypical polyolefins, whether homopolymers or copolymers, in fact, commercial products are generally somewhat more complex and may contain up to ten percent by weight of other, generally hydrocarbon constituents, as part of the polymers or in a mixture exclusive of filler. Commercial examples of such products, all adequately protected in accordance with the invention, are the polymerization products of monomers, such as, ethylene or propylene together with vinyl acetate, acrylic acid, methacrylic acid, and/or esters of acrylic acids.

C. Other Ingredients

A variety of other ingredients are conventionally included in commercial polymeric products of the type contemplated. These include lubricants, fillers, pigments, and other colorants, etc. Under certain circumstances, pigmentation may be designed to afford protection from ultraviolet attack although, in general, stabilizers of the invention are contemplated primarily for use in primary insulation which, in most structures, is protected from ultraviolet attack by outer sheathing.

D. Other Considerations

Stabilizers of the invention have shown substantial effectiveness in protecting polymers from thermal oxidative attack. To a certain extent, these antioxidants are also useful as copper deactivators, thereby suggesting their use in primary insulation over copper conductor. For long term use, however, copper deactivation is not exceptional; and it may be desirable to include additional stabilizers designed to protect against this degradative mechanism. Suitable deactivators are the chemically related compounds described in copending applications Ser. No. 500,958 filed Aug. 27, 1974, now U.S. Pat. No. 3,970,637, and Ser. No. 500,959, filed Aug. 27, 1974, now U.S. Pat. No. 4,014,853, Comments thus far suggest that contemplated use entails intimate contact between the stabilized polymer and an active metal. It is, in fact, expected that use of the inventive materials will largely be as primary insulation. For many uses polyethylene wire insulation stabilized with only one of the materials of the invention may not meet the long life requirement for many purposes, and it may be necessary to include an additional stabilizer—an additional deactivator. Where a copper conductor is used, this is generally contemplated. Where less active metals, such as aluminum are utilized the metal deactivation function may be served adequately by a stabilizer of the invention.

Primary insulated conductor usually included with other conductors within a sheathing is normally color coded for identification purposes. Dyestuffs or pigments, generally in amount of below 0.5 percent by weight, may serve this function. For certain polymeric compositions, further economies may be realized by filler material, such as, silica. In such instances, it is normal practice to specify stabilizers as a percentage of the total composition exclusive of such filler. Other modifiers may serve a variety of usual functions—for example, small amounts of butyl rubber or butadiene may be included to improve low temperature properties or impact resistance. Such modifiers may or may not be stabilized by stabilizers of the invention; and it is occasional practice to include stabilizers for these modifiers. Stabilization, in accordance with the invention, is concerned primarily with the saturated polymeric compound/s and a given amount of stabilizer relative to such saturated polymer has a generally predictable stabilization effect on such compound regardless of other ingredients present.

In common with other stabilized saturated polymeric compositions, stabilizers of the invention are ordinarily contained in amount of up to about 0.1 percent by weight and, generally, never in excess of 0.5 percent by weight. Amounts less than about 0.01 percent are generally inadequate for discriminating use. Maximum limits may be set by desired life and/or by solubility limits.

2. Test Procedure

Compositions were synthesized by condensing one mole of oxalyl dihydrazide with two moles of the appropriate carbonyl compound in a solvent (e.g., ethanol or dimethyl sulfoxide). This is a conventional condensation reaction well understood by workers in the field. Appropriate conditions are evident from standard references such, for example as J. March, "Advanced Organic Chemistry", McGraw Hill, New York, 1968.

Accelerated test procedures utilized to determine effectiveness have been in prevalent use for many years. They generally take the form of oxygen uptake measurement with the polymeric composition at some elevated temperature. For polyethylene compositions chosen as the subject of the examples, uptake measurements were conducted at 140 degrees C. Test procedures are adequately described in the literature. See, for example, W. L. Hawkins, "Polymer Stablization," Wiley, New York, 1972, Chapter 10. Briefly, samples of measured volume are placed in a tube attached to a mercury manometer together with a measured quantity of absorbant material. Tube and associated apparatus are evacuated, flushed with, and finally filled with, oxygen and are brought to temperature in an appropriate furnace. Tube and contents are next connected to an oxygen gas burette; the system is adjusted to zero reading at atmospheric pressure, and readings of oxygen uptake are measured as a difference in column heights. Readings are taken at appropriate intervals, generally several hours apart.

The form of the resultant data is that of the conventional hindered phenol-stabilized system. This is characterized by an initial period known as the induction period in which oxygen uptake is extremely low. The induction period terminates with a sharp increase in slope of oxygen uptake vs. time.

Three forms of tests were conducted. In the first, effectiveness primarily as a metal deactivator was measured; in the second, effectiveness solely as a thermal antioxidant was evaluated; and in the third performance as a composite thermal antioxidant-metal deactivator was evaluated. For comparison purposes, all tests were conducted on a commercial polyethylene composition.

Samples for the first series of tests were prepared by extruding unstabilized polyethylene with 0.1 percent by weight of the inventive stabilizer together with 0.1 percent of a hindered phenolic thermal stabilizer (0.1 percent tetrakis-3-(3,5-di-t-butyl-4-hydroxyphenyl) propionatemethyl methane on 22 gauge copper wire. Insulation thickness in each instance was 6-7 mils. Gross sample weight was approximately 1 gram with about 0.108 gram being contributed by the insulation.

The second series of tests was performed on 0.1 gram, 10 mil thickness film samples of polyethylene, stabilized only by one of the inventive compounds.

In the third series of tests, precisely the same procedure was followed as in the first series except that the hindered phenolic thermal stabilizer was omitted.

The termination of the induction period was set at 1.0 millimeter of oxygen uptake for the 0.1 gram polymer sample. Choice of this particular level is meaningful from the standpoint of mechanical and electrical properties.

3. Examples

Examples are set forth in tabular form with Tables I, II, and III showing effectiveness as copper deactivator, as thermal antioxidant, and as composite metal deactivator--thermal antioxidant, respectively. Each Table includes a "standard" which corresponds with the same polymeric composition, however, without a stabilizer in accordance with the invention. Standards differ from Table to Table, as described under the preceding section. The standard of Table I is the polymer composition plus the selected prior art hindered phenolic antioxidant. The standards of Tables II and III, on the other hand, are unstabilized polymeric material.

Data of Table I show stabilizers of the invention to be reasonably effective as metal deactivators. The same type of accelerated data however indicates a substantially longer protective period for the best of the prior art metal deactivators and it is expected that long life products may include such a prior art stabilizer. For some purposes, however, for example where insulation is in contact with aluminum or other less active metal, incorporation of a prior art metal deactivator may not be required.

Example 3, Table II, is most significant. The induction period for the chosen inventive stabilizer is 280 hours. By comparison a prevalently used prior art antioxidant, thought most effective by many workers, results in a protective period of only 196 hours.

From Table III it is seen that the selected inventive stabilizer is quite effective as a composite metal deactivator-thermal antioxidant. For many purposes it will be unnecessary to include any other stabilizer. Where longer life is required, it is expected that the additional stabilizer should take the form of a metal deactivator. An appropriate metal deactivator is a related compound of the class set forth in copending application Ser. No. 500,958 filed Aug. 27, 1974 now U.S. Pat. No. 3,970,637. Alternatively, a commercially available metal deactivator may be utilized.

TABLE I

Effectiveness as Metal Deactivator

| Example | Conventional Antioxidant | Inventive Stabilizer | Induction Period at 140° C - Hours |
|---|---|---|---|
| 1 | (HO—[di-t-butyl phenyl]—C—C—C—O—C(=O))$_4$C | (HO—[di-t-butyl phenyl]—C(=N—NH—C(=O)))$_2$ | 48 |
| 2 | " | (HO—[3,5-dimethoxy phenyl]—C(CH$_3$)=N—NH—C(=O))$_2$ | 50 |
| Standard | " | NONE | <5 |

TABLE II

Effectiveness as Thermal Antioxidant

| Example | Inventive Stabilizer | Induction Period at 140 C - Hours |
|---|---|---|
| 3 | (HO—[di-t-butyl phenyl]—C(H)=N—NH—C(=O))$_2$ | 280 |
| Standard | NONE | 4.5 |

Note: For comparison purposes, Example 3 was rerun, however, using the conventional antioxidant of Table I, in lieu of an inventive stabilizer. The oxygen uptake period was 196 hours. This prior art antioxidant has been commercially available for some time and is in prevalent use for discriminating long life applications.

TABLE III
Effectiveness as Composite Metal Deactivator - Thermal Antioxidant

| Example | Inventive Stabilizer | Induction Period at 140 C - Hours |
|---------|---------------------|-----------------------------------|
| 4       | 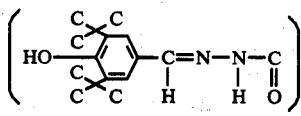 | 48 |
| Standard | NONE | 4.5 |

As a further comparision, Example 4 was rerun, however, substituting the conventional antioxidant of Table I, for the inventive stabilizer indicated. The induction period at 140° C was less than 5 hours.

What is claimed is:

1. A composition consisting essentially of a polymeric composition, the said polymeric composition exclusive of filler being at least 90 percent by weight of essentially saturated polyolefin polymer selected from the group consisting of homopolymers and copolymers, said polymer containing a stabilizer composition characterized in that the said stabilizer composition contains only one thermal oxidation stabilizer, said thermal oxidation stabilizer consisting essentially of at least one compound chosen from the group consisting of compounds in accordance with the formula

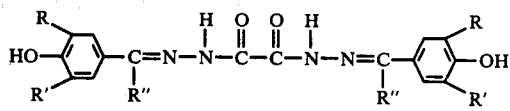

in which R is an alkyl substituent containing a tertiary carbon, said tertiary carbon being attached directly to the phenyl ring, in which R' is hydrogen or an alkyl substituent which may also contain a tertiary carbon, and in which R" is hydrogen or an alkyl substituent, and in which any of the phenyl hydrogens bonded directly to either of the phenyl rings may be replaced by a hydrocarbon substituent, wherein said saturated polyolefin polymer contains a percentage by weight of said thermal oxidation stabilizer in the range of .01 to 0.5.

2. Composition of claim 1 in which R is tertiary butyl.

3. Composition of claim 2 in which R' is tertiary butyl.

4. Composition of claim 1 in which R' is O—CH$_3$.

5. The composition of claim 1 wherein said saturated polyolefin polymer is made from monomers selected from the group consisting essentially of ethylene and propylene.

* * * * *

UNITED STATES PATENT AND TRADEMARK OFFICE
CERTIFICATE OF CORRECTION

PATENT NO. : 4,073,771

DATED : February 14, 1978

INVENTOR(S) : Ray L. Hartless and Anthony M. Trozzolo

It is certified that error appears in the above-identified patent and that said Letters Patent are hereby corrected as shown below:

Column 1, line 28, "materials" should read --metals--. Column 1, line 40, "Catalysts" should read --Catalysis--. Column 1, line 68, "5, Polymer Engineering and Science" should be in italics. Column 3, line 20, "tiarybutyl" should read --tiary-butyl--. Column 5, line 54, "millimeter" should read --milliliter--.

Signed and Sealed this

Eleventh Day of July 1978

[SEAL]

Attest:

RUTH C. MASON
*Attesting Officer*

DONALD W. BANNER
*Commissioner of Patents and Trademarks*